United States Patent [19]

Mrowca

[11] Patent Number: 5,523,405
[45] Date of Patent: Jun. 4, 1996

[54] PREPARATION OF 4,6-DIMETHOXY-2-((PHENOXYCARBONYL) AMINO)-PYRIMIDINE

[75] Inventor: Joseph J. Mrowca, Wilmington, Del.

[73] Assignee: E. I. Du Pont de Nemours and Company, Wilmington, Del.

[21] Appl. No.: 404,215

[22] Filed: Mar. 14, 1995

[51] Int. Cl.$^6$ ............................................. C07D 239/52
[52] U.S. Cl. ............................................................ 544/321
[58] Field of Search ............................................... 544/321

[56] References Cited

U.S. PATENT DOCUMENTS

| | | | |
|---|---|---|---|
| 5,017,212 | 5/1991 | Ishida et al. | 71/92 |
| 5,102,444 | 4/1992 | Liang | 71/92 |

*Primary Examiner*—John M. Ford

[57] ABSTRACT

Process for preparing 4,6-dimethoxy-2-((phenoxycarbonyl)amino-pyrimidine comprising reacting 2-amino-4,6-dimethoxy pyrimidine and phenyl chloroformate in an inert solvent in the presence of an acid receptor.

10 Claims, No Drawings

PREPARATION OF 4,6-DIMETHOXY-2-((PHENOXYCARBONYL) AMINO)-PYRIMIDINE

BACKGROUND OF THE INVENTION

The present invention pertains to a process for the preparation of an intermediate chemical compound useful for preparing herbicides. More specifically, the present invention pertains to an improved process for preparing 4,6-dimethoxy-2-((phenoxycarbonyl)amino)-pyrimidine (hereinafter "DPAP") which is useful as an intermediate for the preparation of sulfonylurea herbicides.

Intermediates for herbicides are preferably free of substantial amounts of impurities especially impurities which will be carried through to the final herbicide itself. Impurities in agricultural products come under careful regulatory scrutiny and are subject to severe restrictions. Therefore, advantageous methods for making intermediates are not only advantageous for producing high yields but also are advantageous for producing the intermediate in high purity "as made" so that little, preferably no, further purification is needed. Accordingly, an object of this invention is to provide a method for making DPAP in high yield and high purity.

References U.S. Pat. Nos. 5,102,444 and 5,017,212 disclose the preparation of DPAP and use of same in the preparation of sulfonylurea herbicides, but do not disclose the present invention.

SUMMARY OF THE INVENTION

A process has now been discovered that results in the preparation of 4,6-dimethoxy-2-((phenoxycarbonyl)amino)-pyrimidine in high yields and in high purity. Accordingly, the process of the invention to prepare 4,6-dimethoxy-2-((phenoxycarbonyl)amino)-pyrimidine comprises reacting 2-amino-4,6-dimethoxypyrimidine and phenyl chloroformate in an inert solvent in the presence of an acid receptor at a temperature of between 10° to 45° C.

DETAILS OF THE INVENTION

The process of the invention comprises reacting 2-amino-4,6-dimethoxypyrimidine and phenyl chloroformate in an inert solvent selected from 1,4-dioxane and tetramethylurea in the presence of N,N-dimethylaniline at a temperature of 10° to 45° C.

The preferred solvent is 1,4-dioxane.

The amount of phenyl chloroformate is generally at least stoichiometric. The preferred amount of phenylchloroformate is 10–75% excess of the stoichiometric amount.

The acid receptor, N,N-dimethylaniline, is generally present in an equal molar amount to the phenyl chloroformate.

The preferred reaction temperature is in the range of 20° to 30° C. Pressure is not controlled and is ambient atmospheric pressure.

In a typical operation, the 2-amino-4,6-dimethoxypyrimidine, solvent and acid receptor are admixed in a reactor equipped with a stirrer and means for cooling the reaction. Phenyl chloroformate is added to the stirred reaction mixture which is maintained at the desired temperature. The rate of addition of the phenyl chloroformate is not critical and can be any convenint rate which allows the desired reaction temperature to be maintained. The starting 2-amino-4,6-dimethoxypyrimidine and product DPAP are not substantially dissolved in the solvent and are present in the reaction mixture as a slurry. Sometimes the DPAP forms a supersatuated solution which can be induced to crystallize by introducing seed crystals of same. After addition of all ingredients, the reaction mixture is held at reaction temperature generally for about 4 to 24 h, then quenched with water. The product is recovered by filtration, washed with water (and optionally isopropanol) and dried at an elevated temperature, generally about 55° C, under vacuum.

The impurity, N,N'-bis(4,6-dimethoxy-2-pyrimidinyl)urea, is recovered with the product DPAP in the filtration step. The present process, however, produces low levels of this impurity so that little, if any, further purification of the product DPAP is needed. Reducing the amount of or eliminating product purification is advantageous because extra purification steps and loss of product thereto is avoided.

It has been found that the product yield and the amount of N,N'-bis(4,6-dimethoxy-2-pyrimidinyl)urea impurity formed is critically dependent on the choice of solvent and acid receptor. The present process employing 1,4-dioxane or tetramethylurea solvents and N,N-dimethylaniline acid receptor provides substantially higher yield and lower N,N'-bis(4,6-dimethoxy-2-pyrimidinyl)urea impurity than the prior art processes of U.S. Pat. Nos. 5,102,444 and 5,017,212 wherein the solvent is tetrahydrofuran and the acid receptor is dimethylpyridine.

Adding phenyl chloroformate in excess is also believed to be helpful in keeping the N,N'-bis(4,6-dimethoxy-2-pyrimidinyl)urea impurity low. Any benefit of adding excess phenyl chloroformate is believed to be separate from and in addition to any effect of solvent and acid receptor on yield and purity.

This following examples illustrate the present invention and the advantage thereof.

EXAMPLE 1

A 500 mL flask was charged with 23.8 g (0.154 mol) of 2-amino-4,6-dimethoxypyrimidine, 29.1 g (0.240 mol) of N,N-dimethylaniline, and 110 mL 1,4-dioxane. The mixture was cooled to 5° C. with an ice bath. Then 37.58 g (0.24 mol) of phenyl chloroformate was added dropwise while keeping the temperature of the reaction mixture below 20° C. The reaction mixture was stirred for 16 h at ambient room temperature (20° to 25° C.) and then cooled back down to 5° C. Water, 325 mL, was added to the reaction mixture; the temperature during addition was kept below 20° C. The reaction mixture, a slurry, was filtered and the solids washed twice with an additional 50 mL of water. Solids were dried by suction through the filter. Weight of recovered solids having a melting point of 117°–120° C. was 34.24 g which calculates to an 81% yield, uncorrected for purity.

EXAMPLE 2

The procedure of Example 1 was repeated except that 110 mL of tetramethylurea was used in place of 1,4-dioxane. Weight of recovered solids having a melting point of 119°–122° C. was 35.77 g which calculates to an 85% yield, uncorrected for purity.

EXAMPLE A (COMPARATIVE)

This demonstrates the use of tetrahydrofuran (THF) solvent with N,N-dimethylaniline acid receptor. Yield was lower than Examples 1 and 2. Product purity, as judged by the lower melting point range, was also lower.

A 500 mL flask was charged with 23.8 g of 2-amino-4,6-dimethoxypyrimidine, 29.10 g of N,N-dimethylaniline and 110 mL of THF. The mixture was cooled to 5° C. with an ice bath and 37.58 g phenyl chloroformate was added slowly while keeping the temperature below 20° C. After stirring 16 h at ambient room temperature (20°–25° C.), the mixture was cooled to 5° C. Water, 360 mL, was added to the reaction mixture slowly while keeping the temperature below room temperature. The reaction mixture, a slurry, was filtered and the solids washed with two 50 mL aliquots of water. Solids were dried on the filter then placed in a pan to air dry. Weight of recovered solids having a melting point of 114°–117° C. was 22.93 g which calculates to a 54% yield, uncorrected for purity.

EXAMPLE 3

A 250 mL flask was charged with 15.6 g (0.101 mol) of 2-amino4,6-dimethoxypyrimidine, 20 mL (0.158 mol) of N,N-dimethylaniline, 50 mL of 1,4-dioxane, and 20 mL (0.159 mole) of phenyl chloroformate. The mixture was stirred for 2 h at room temperature (20°–25° C.) and then allowed to stand 16 hours at the same temperature. The reaction mixture was transferred to a separate flask containing 140 mL of water. An oil formed which eventually crystallized. The reaction mixture was faltered and the solids were washed with three 50 mL aliquots of water, and two 25 mL aliquots of isopropanol. Solids were dried by pulling air through the falter. The melting point was 122°–123° C. Assay of the solids: 96.9% 4,6-dimethoxy-2-((phenoxycarbonyl)amino)pyrimidine, 1.54% 2-amino-4,6-dimethoxypyrimidine and 0.20% N,N'-bis(4,6-dimethoxy-2-pyrimidinyl)urea. A total of 22.8 g of solids were recovered for a yield, corrected for purity, of 79.8%.

EXAMPLE B (COMPARATIVE)

This demonstrates 2,6-dimethylpyridine acid receptor with 1,4-dioxane solvent. Yield and purity are lower than Example 3.

Example 3 was repeated except that 19 mL (0.163 mol) of 2,6-dimethylpyridine was used in place of the 20 mL of N,N-dimethylaniline. The melting point of the product was 115°–117° C. Assay was 85.7% 4,6 dimethoxy-2-((phenoxycarbonyl)amino)pyrimidine, 0.47% 2-amino4,6-dimethoxypyrimidine and 1.14% N,N'-bis(4,6 -dimethoxy-2-pyrimidinyl)urea. A total of 24.8 g of solids was recovered for a yield, corrected for purity, of 76.8%.

EXAMPLE C (COMPARATIVE)

This demonstrates 2,6-dimethylpyridine acid receptor with THF solvent. Again, the purity is lower than Example 3. Yield was not calculated because some product spilled during handling before it was weighed.

Example B was repeated except that 50 mL of THF was used in place of the 1,4-dioxane. The melting point of the product was 118°–120° C. Assay: 90.6% 4,6-dimethoxy-2-((phenoxycarbonyl)amino)pyrimidine, 1.11% 2-amino4,6dimethoxypyrimidine and 2.13% N,N'-bis(4,6-dimethoxy-2-pyrimidinyl)urea.

EXAMPLE 4

Charged is 120 kg of 1,4-dioxane, 59.1 kg (488 mol) of N,N-dimethylaniline, and 47.7 kg (308 mol) of 2-amino-4,6-dimethoxypyrimidine to a 100 gallon reactor. Phenyl chloroformate, 76.4 kg (488 mol), is added over 1.5 h while the temperature is kept at 25° C. by jacket cooling. Three hours after the end of the phenyl chloroformate addition, the reaction mass is seeded with a small quantity of previously prepared DPAP crystals. After another 30 minutes, the reaction mass is seeded again. Agitation at 25° C. is continued for another 11 h. The reaction slurry is then transferred to a 300 gallon reactor that already contains 159 kg of water; the temperature in this reactor is kept below 35° C. by both adjusting the transfer rate of the reaction slurry and the jacket cooling of the 300 gallon reactor. The 100 gallon reactor and transfer line are then rinsed with 11.4 kg of 1,4-dioxane. The resulting slurry is stirred for another 30 min before an additional 280 kg of water is added. Stirring is continued for 30 min before the slurry is discharged to filters. The reactor is rinsed with water followed by isopropanol, the rinsings being used to wash the filter cakes. The product is then dried at 55° C. under a vacuum of 100 mm Hg or less.

This procedure was followed for 23 batches and the average purity of all batches was 97.1%. The overall average yield, corrected for purity, was 88.3%.

What is claimed is:

1. In a process for the preparation of 4,6-dimethoxy-2-((phenoxycarbonyl)amino)pyrimidine by reacting 2-amino-4,6-dimethoxy pyrimidine and phenyl chloroformate the improvement comprising carrying out the reaction in at least stoichiometric amounts in an inert solvent selected from 1,4-dioxane and tetramethylurea and in the acid receptor N,N-dimethylaniline at a temperature of from 10° to 45° C.

2. The process of claim 1 wherein the solvent is 1,4-dioxane.

3. The process of claim 1 wherein the solvent is tetramethylurea.

4. The process of claim 1 wherein the temperature is 20°–30° C.

5. The process of claim 4 wherein the solvent is 1,4-dioxane.

6. The process of claim 4 wherein the solvent is tetramethylurea.

7. The process of claim 1 wherein the amount of phenyl chloroformate is 10–75% in excess of the stoichiometric amount.

8. The process of claim 7 wherein the temperature is 20°–30° C.

9. The process of claim 7 wherein the solvent is 1,4-dioxane.

10. The process of claim 7 wherein the solvent is tetramethylurea.

* * * * *